United States Patent [19]

Pussard née Contant et al.

[11] Patent Number: 5,472,851

[45] Date of Patent: Dec. 5, 1995

[54] METHOD OF DETERMINING A PLASMINOGEN ACTIVATOR AND ITS INHIBITOR

[75] Inventors: Geneviève Pussard née Contant, Courbevoie; Jean-Luc Martinolli, Villeneuve la Garenne; Gérad Quentin, Colombes, all of France

[73] Assignee: Serbio, France

[21] Appl. No.: 698,314

[22] Filed: May 10, 1991

[30] Foreign Application Priority Data

May 10, 1990 [FR] France ................... 90 05808

[51] Int. Cl.⁶ ............... C12Q 1/56; C12N 9/72; C12P 21/06; A01N 37/18
[52] U.S. Cl. ............ 435/13; 435/215; 435/212; 435/219; 435/188; 435/69.2; 424/94.3; 514/2; 530/350
[58] Field of Search .............. 435/13, 215, 212, 435/219, 188, 69.2; 514/2; 424/94.3; 530/350

[56] References Cited

U.S. PATENT DOCUMENTS

| | | | |
|---|---|---|---|
| 4,629,694 | 12/1986 | Harpel | 435/215 |
| 4,640,835 | 2/1987 | Shimizu et al. | 435/215 |
| 4,661,453 | 4/1987 | Pollard | 435/215 |
| 4,752,603 | 6/1988 | Collen et al. | 514/2 |
| 4,837,022 | 6/1989 | Kakimoto et al. | 435/215 |
| 4,999,194 | 3/1991 | Broeze et al. | 435/212 |
| 5,073,626 | 12/1991 | Wun | 435/215 |

OTHER PUBLICATIONS

Zubay; "Biochemistry"; pp. 764 and 810; (1983).
Kress; Hemostasis and Animal Venoms; "The Action of Snake Venom Metalloproteinases of Plasma Proteinase Inhibitors", pp. 335–348.

Primary Examiner—David A. Redding
Assistant Examiner—Louise N. Leary
Attorney, Agent, or Firm—Ostrolenk, Faber, Gerb & Soffen

[57] ABSTRACT

The present invention relates to the use of a substance which inhibits the plasma proteins $\alpha_2$-AP and/or $\alpha_2$-M in the field of the determination and assay of plasminogen activators and inhibitors of said plasminogen activators. It relates in particular to a method of determining (i) a plasminogen activator selected from the group consisting of tissue plasminogen activators (tPAs) and urokinase plasminogen activators (uPAs), and (ii) an inhibitor (PAI) of said plasminogen activator, said method, which involves converting plasminogen to plasmin and then assaying the plasmin resulting from said conversion, comprising inhibition of the plasma proteins $\alpha_2$-antiplasmin and/or $\alpha_2$-macroglobulin by means of a substance selected from the group consisting of metalloproteinase materials.

8 Claims, 9 Drawing Sheets

METHOD OF DETERMINING A PLASMINOGEN ACTIVATOR AND ITS INHIBITOR

FIELD OF THE INVENTION

The present invention relates to a novel technical solution for the determination or assay of, on the one hand, a plasminogen activator selected from the group consisting of tissue and urokinase plasminogen activators, and, on the other hand, an inhibitor of said plasminogen activator.

It relates to the method of determining a plasminogen activator and its inhibitor, which, according to said novel solution, comprises the inhibition of two plasma proteins: $\alpha_2$-antiplasmin ($\alpha_2$-AP) and $\alpha_2$-macroglobulin ($\alpha_2$-M).

PRIOR ART

The activities of tissue plasminogen activators (tPAs) and urokinase plasminogen activators (uPAs) are regulated by an inhibitory substance called plasminogen activator inhibitor (PAI). It is known in particular that tPAs and PAIs play a very important role in the regulation of fibrinolysis and that the previously known methods of assaying them are based on the principle of measuring the plasmin generated in the system from the plasminogen by means of a plasmin-specific (fluorogenic or, preferably, chromogenic) peptide substrate.

The purpose of fibrinolysis is to restore vascular permeability by degrading the fibrin deposits which are liable to form on the vessel walls. Fibrinolysis is effected by plasmin, which is a very powerful enzyme circulating in the plasma in its inactive form: plasminogen.

There are two routes by which plasminogen can be activated to form plasmin: a so-called intrinsic (or endogenous) route and a so-called extrinsic (or exogenous) route. In vivo, fibrinolysis is perpetually regulated by a system of inhibitors so that the fluidity of the blood is always maintained. For information, the mechanisms of fibrinolysis have been illustrated schematically in FIG. 1 below, showing the intervention of the activators and inhibitors. In FIG. 1, every arrow which is a thick continuous line denotes an activation and every arrow which is a thick broken line denotes an inhibition.

Urokinase [also called urokinase plasminogen activator (abbreviated to uPA)] is involved in the mechanisms (intrinsic route) of fibrinolysis initially in the form of prourokinase [called single-chain urokinase plasminogen activator (abbreviated to scuPA)] and then in the form of so-called high molecular weight urokinase [also called two-chain urokinase plasminogen activator (abbreviated to tcuPA or HMW-UK)]. tPA is involved in the mechanisms (extrinsic route) of fibrinolysis in the form of sctPA [called single-chain tissue plasminogen activator (also abbreviated in the literature to tPA-I)] and in the form of tctPA [called two-chain tissue plasminogen activator (also abbreviated in the literature to tPA-II)].

However, it should be pointed out that, in the physiological state, scuPA (intrinsic route) seems to be largely responsible for the fibrinolytic activity and tPA (extrinsic route) is only involved to a small extent [about 95% of the tPA is rapidly complexed by PAI-1 as soon as it is released; only about 5% of the tPA remains in the free and hence active form in the plasma]. On the other hand, as soon as the organism is subjected to any kind of attack, the extrinsic route then plays a predominant and essential role in mitigating the excessive formation of plasmin.

tPA is principally released from the endothelial cells. It can be extracted from various tissues of animal origin (pig's ovary and heart) or human origin (uterus). However, as the amount of purified tPA extracted from these tissues is minute, the preferred main source of purified tPA is derived from the cell culture of human melanomas (BOWES). By virtue of this cell culture, which secretes large amounts of tPA, it has been possible to obtain purified tPA, estimate its molecular weight, determine its biochemical structure and characterize its physiological activities. tPA is a serine protease with an average molecular weight of about 70,000 daltons, which is capable of converting plasminogen to plasmin. The presence of fibrin permits optimum activation of plasminogen by tPA.

Plasminogen activator inhibitor [abbreviated to PAI] is involved in the regulation of plasminogen activators. Essentially four forms of PAI are known, namely PAI-1 (inhibitor 1 of plasminogen activators), PAI-2 (inhibitor 2 of plasminogen activators), PAI-3 (inhibitor 3 of plasminogen activators) and the protease nexine [see Thrombosis and Haemostasis, 56 (n° 3), pages 415–416, (1986)].

tPA inhibitors, which are also called antiactivators, are mainly of two types:

PAI-1, which is present in the plasma and the alpha granules of the platelets and reacts with both tPA and urokinase to give inactive complexes: (tPA-PAI-1) and (uPA-PAI-1); as the rate of complexation is very high, the fact that free PAI-1 exists in a plasma implies that there cannot be active free tPA in this plasma; and PAI-2, which is probably of macrophagic origin, is at its maximum concentration in pregnant women in the 3rd term of pregnancy and, although it forms inactive complexes with tPA, possesses a greater affinity towards uPA [see E. D. SPRENGERS et al., Blood, 69 (n° 2), pages 381–387, (1987)].

In other words, it is known that the activities of tissue and urokinase plasminogen activators are regulated by at least two specific inhibitors of the endothelial type (PAI-1) and placental type (PAI-2) and that the pairs tPA/PAI and uPA/PAI play an essential role in the regulation of fibrinolysis.

It is further known that the antiplasmin activity of plasma, which is very high, is located mainly in the $\alpha_1$-globulins and $\alpha_2$-globulins. Six plasma proteins are known which are capable of inhibiting plasmin in a purified system; these are:

$\alpha_1$-antitrypsin,
inter-$\alpha$-antitrypsin,
the inhibitor of C1 esterase (abbreviated to C1-Inh),
antithrombin III (abbreviated to AT III),
$\alpha_2$-macroglobulin (abbreviated to $\alpha_2$-M), and
$\alpha_2$-antiplasmin (abbreviated to $\alpha_2$-AP).

In the presence of normal plasma concentrations of $\alpha_2$-AP and $\alpha_2$-M, the other plasmin inhibitors are only involved to a small extent in the inactivation of the plasmin. The role of $\alpha_2$-M is to inhibit the excess plasmin when there is no longer any free $\alpha_2$-AP. These inhibitors—mainly $\alpha_2$-AP and $\alpha_2$M—interfere significantly in PAI assays [see the article by G. CONTANT et al., Thrombosis Research, 56, pages 377–386, (1989) and the paper by W. KAUSEL et al. delivered at the Congrès de la Ligue Méditerranénne de Lutte contre la Thrombose, Athens, 1988, and entitled: "Relative Contribution of Known Plasminogen Activator Inhibitors (PAIs) to the tPA and uPA Inhibitory Capacity of Plasma"].

The methods which have already been recommended for the assay of tPA and PAI are illustrated schematically in Diagrams A and B below. They are based on measurement of the plasmin generated in the system by means of a plasmin-specific substrate.

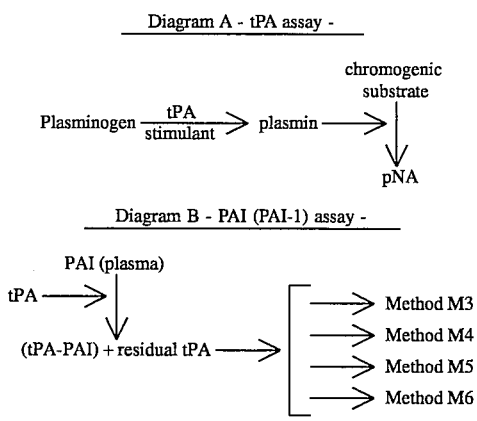

It is known in particular that, in the past, the recommended methods of assaying the biological activity of tPA have been in the solid phase and in the liquid phase.

In the solid phase (method M1), a technique is known which is based on the fixing of a network of fibrin to the surface of cups in a microplate; after the source of tPA has been fixed, washes are carried out in order to remove most of the factors hindering the generation of plasmin. This technique has advantages:

any source of tPA can be used, such as plasma, the measured activity is specific for tPA and independent of prourokinase [abbreviated to scuPA] and urokinase [abbreviated to tcuPA].

In this context, see the modalities of method M1 described by E. ANGLES-CANO et al., "A Spectrophotometric Solid-Phase Fibrin-Tissue Plasminogen Activator Activity Assay (SOFIA-tPA) for High Fibrin Affinity Tissue Plasminogen Activators", Anal Biochem., 153, pages 201–210, (1986).

In the liquid phase (method M2), a technique is known wherein excess plasminogen and soluble fibrinogen fragments, as a stimulant, are added to the source of tPA to be assayed. The excess plasmin generated cleaves the plasmin-specific substrate [for example one of the substrates CBS 30.41 (H—D—Abu—L—CHA—L—Lys—pNA) or CBS 33.08 (H—D—Nle—L—CHA—L—Arg—pNA) marketed by DIAGNOSTICA STAGO] and releases pNA, which can be detected (particularly at 405 nm). The source of tPA can be either purified tPA (extracted from melanoma as indicated above) which is used for calibration, or plasma euglobulins (1/10 dilution at pH 5.9), i.e. a source of tPA devoid of plasmin inhibitors (especially $\alpha_2$-AP) which would hinder the second step of the reaction.

Method M2 is illustrated in the leaflet for the assay "STACHROM PA" from DIAGNOSTICA STAGO (reference n° 0822 in this Company's catalog).

The measured activity is particularly associated with tPA by virtue of the fibrinogen fragments, but it is amplified by the other activation routes (Factor XII, prourokinase, urokinase). For the measurement of the activity to be specific for tPA, it is necessary to add anti-tPA antibodies.

Another method (method M7) is also known which consists in separating out the free tPA by adsorption on a column of lysine-sepharose, and which has been described by E. GYZANDER et al., Thromb. Res., 35, pages 547–548, (1984).

The methods which can be applied to the assay of PAI can also be applied to the assay of tPA since they are based on determination of the residual tPA after complexation of the PAI contained in the plasma to be tested. They include especially method M3 described by C. KORNINGER et al., Thromb. Haem., 46, pages 622–665, (1981) and 52, pages 127–130, (1984), which uses euglobulins; method M4 described by J. CHMIELEWSKA et al., Thromb. Res., 31, pages 427–436, (1983), which uses acidified plasma; method M5 described by J. H. VERHEIJEN et al., Thromb. Haem., 48, pages 266–269, (1982), which involves the precipitation of euglobulins on pure or dilute plasma; and method M6 described in the afore-mentioned article by G. CONTANT et al., which is used in the assay kit marketed under the name "STACHROM PAI" (reference n° 0824) by DIAGNOSTICA STAGO. For the afore-mentioned technique of G. CONTANT et al. to be specific, it is important to dilute the test sample in plasma which is depleted (i.e. impoverished or exhausted) in PAI, in which case interference by the plasmin inhibitors (other than $\alpha_2$-AP and $\alpha_2$-M) contained in the plasma becomes negligible.

The main disadvantage of the afore-mentioned methods of assaying tPA and/or PAI is the need to separate the free tPA from the tPA-PAI and uPA-PAI complexes and to prevent the action of the plasmin inhibitors (more particularly $\alpha_2$-AP and $\alpha_2$-M) by acidification of the plasma (see method M4), precipitation of the euglobulins (see method M5), or adsorption on a column (see method M7).

To summarize, previously known methods M1–M7 are long and difficult to carry out and are liable to be deficient in terms of the reproducibility and/or sensitivity of the assays.

Furthermore, as the inactivation of $\alpha$-antiplasmins by oxidation is known, especially from the article by D. JOHNSON et al., J. Biol. Chem., 254, pages 4022–4026, (1979), from abstract n° 01358 of the communication by D. LAWRENCE et al. (Congress on "Thrombosis and Haemostasis", San Diego, 1985) and from the article by D. LAWRENCE et al., Biochem., 25, pages 6351–6355, (1986), by means of chloramine T, it is known that a novel method (method M8) has been proposed which consists in adding an oxidizing agent specific for methionine groups, such as chloramine T, in order to inhibit the action of $\alpha_2$-AP. [In this context, see the articles by T. W. STIEF et al., Thromb. Res., 49, pages 581–589, (1988), 50, pages 559–573 (1988), and 56, pages 213–220, (1989), published European patent application EP-A-0 297 597 and the leaflet for the assay kit marketed by BEHRING DIAGNOSTIKA under the name "PAI-TEST", entitled "FUNKTIONELLE BESTIMMUNG DES pLASMINOGEN-AKTIVATOR-IN-HIBITORS" ("FUNCTIONAL DETERMINATION OF PLASMINOGEN ACTIVATOR INHIBITOR") (November 1988)]. As chloramine T and the other oxidizing agents are difficult products to handle, a need has arisen for a novel technical solution for the determination of tissue and urokinase plasminogen activators, on the one hand, and their inhibitors, on the other, which uses different means from those recommended hitherto.

AIM OF THE INVENTION

The novel technical solution which is recommended according to the invention for the determination of a plasminogen activator selected from the group consisting of tissue and urokinase plasminogen activators, on the one hand, and an inhibitor of said plasminogen activator, on the other, is based on the use of a novel means which inhibits or annihilates the plasmin inhibitors $\alpha_2$-AP and/or $\alpha_2$-M.

More precisely, the present invention is based on the surprising discovery that snake venoms containing a metalloproteinase material which inhibits $\alpha_2$-AP and/or $\alpha_2$-M, as described in the article by L. F. KRESS entitled "The Action of Snake Venom Metalloproteinases on Plasma Proteinase Inhibitors", published in Hemotology 7, Basel, pages 335–348, neither degrade nor destroy tissue and urokinase plasminogen activators, on the one hand, or their inhibitors, PAI, on the other.

The novel technical solution according to the invention makes it possible to mitigate the aforementioned disadvantages of the previous assay methods referred to above.

According to a first feature of the invention, a novel technical solution for the determination of plasminogen activators and their inhibitors is proposed which uses at least one metalloproteinase material.

According to a second feature of the invention, a method of determining tissue plasminogen activators (tPAs) and their inhibitors (PAI) is recommended which uses a metalloproteinase material.

According to another feature of the invention, an assay kit is recommended which comprises at least one metalloproteinase material as a reagent.

SUBJECT OF THE INVENTION

According to the invention, a novel use is proposed for a substance which inhibits the plasma proteins $\alpha_2$-antiplasmin and/or $\alpha_2$-macroglobulin in the field of the assay of plasminogen activators and inhibitors of said plasminogen activators, wherein said substance which inhibits said plasma proteins is selected from the group consisting of metalloproteinase materials.

Also according to the invention, a novel method is proposed for determining (i) a plasminogen activator selected from the group consisting of tissue plasminogen activators (tPAs) and urokinase plasminogen activators (uPAs), and (ii) an inhibitor (PAI) of said plasminogen activator, said method, which involves conversion of the plasminogen to plasmin followed by assay of the plasmin resulting from said conversion, comprising inhibition of the plasma proteins $\alpha_2$-antiplasmin and/or $\alpha_2$-macroglobulin by means of a substance selected from the group consisting of metalloproteinase materials.

BRIEF DESCRIPTION OF THE INVENTION

FIG. 1 schematically illustrates the mechanisms of fibrinolysis.

ABBREVIATIONS

Figure 1:
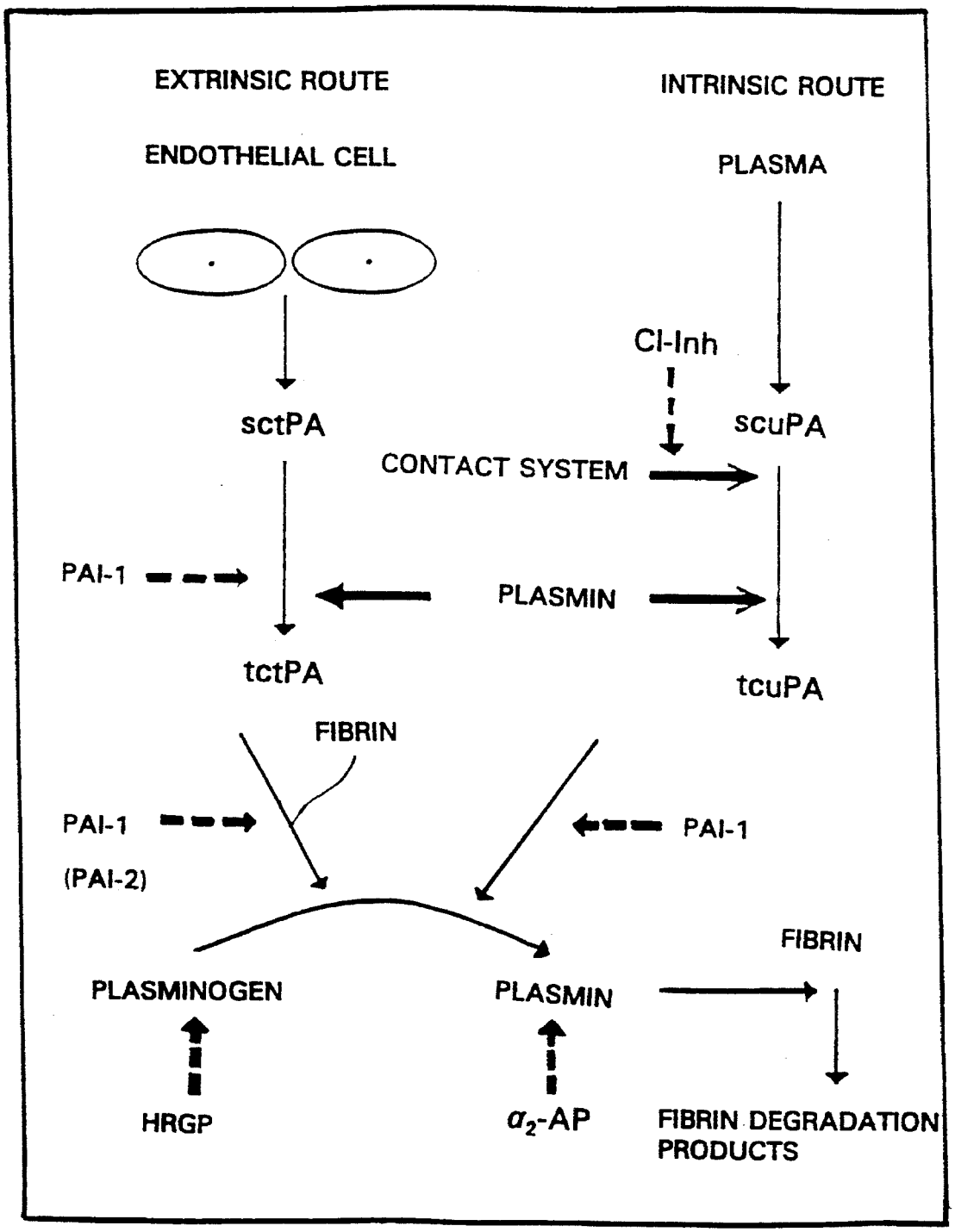

For convenience, the following abbreviations have been used in the present description:

a) relating to fibrinolysis:
$\alpha_2$-AP=$\alpha_2$-antiplasmin
Cl—Inh=inhibitor of Cl esterase
$\alpha_2$-M=$\alpha_2$-macroglobulin
tPA=tissue plasminogen activator
sctPA=single-chain tissue plasminogen activator; alternative nomenclature: tPA-I
tctPA=two-chain tissue plasminogen activator; alternative nomenclature: tPA-II
uPA=urokinase plasminogen activator; alternative nomenclatures: urokinase or urinary plasminogen activator
scuPA=single-chain urokinase plasminogen activator; alternative nomenclature: prourokinase
tcuPA=two-chain urokinase plasminogen activator; alternative nomenclatures: high molecular weight urokinase or HMW-UK
PAI=plasminogen activator inhibitor
PAI-1=inhibitor 1 of plasminogen activators, a substance forming complexes (tPA—PAI—1) and (uPA—PAI—1) with tPA and uPA respectively
PAI-2=inhibitor 2 of plasminogen activators, a substance forming complexes with tPA and uPA
PAI-3=inhibitor 3 of plasminogen activators, a substance capable of forming complexes with uPA
UK=urokinase (alternative nomenclature for uPA)
b) relating to peptide substrates:
Arg=arginyl
Abu=2-aminobutyryl
CHA=3-cyclohexylalanyl
CHT=3-(4-hydroxycyclohexyl)alanyl
Glu=glutaminyl
Gly=glycyl
Hyp=hydroxyprolyl (3Hyp or 4Hyp)
3Hyp=3-hydroxyprolyl (or 3-hydroxypyrrolidine-2-carbonyl)
4Hyp=4-hydroxyprolyl (or 4-hydroxypyrrolidine-2-carbonyl)
Leu=leucyl
Lys=lysyl
Nle=norleucyl
Nva=norvalyl
Phe=phenylalanyl
Phg=phenylglycyl
Pip=pipecolinoyl
Pro=prolyl
Pyr=pyroglutaminyl (or pyrrolid-2-one-5-carbonyl)
Tyr=tyrosyl
Val=valyl
c) other abbreviations:
AMCHA=tranexamic acid; systematic nomenclature: 4-(aminomethyl)cyclohexanecarboxylic acid
BSA=bovine serum albumin
Bzl=benzyl
EACA=$\epsilon$-aminocaproic acid
EM=ethoxymalonyl (EtO—CO—CH$_2$—CO)
Et=ethyl
Me=methyl
MM=methoxymalonyl (MeO—CO—CH$_2$—CO)
OD=optical density
OtBu=t-butoxy
PEG$_n$=polyethylene glycol residue of MW=n
MW=molecular weight
pNA=p-nitroanilino [or (4—NO$_2$)C$_6$H$_4$NH]
RT=room temperature (15°–20° C.)

DETAILED DESCRIPTION OF THE INVENTION

According to the invention, the expression "metalloproteinase material" is understood as meaning a substance consisting of one or more metalloproteinases or a substance containing at least one metalloproteinase. The purpose of the metalloproteinase material used according to the invention is to annihilate, inhibit or destroy the plasma proteases $\alpha_2$-AP and/or $\alpha_2$-M.

Venoms may be mentioned in particular among the metalloproteinase materials which are suitable according to the invention. Venoms containing at least one metalloproteinase can be used either as collected from snakes or insects in particular, or in purified form. Among the snake venoms which can be used, those obtained from animals belonging to the families of the Viperidae and the Crotalidae may be mentioned in particular.

The preferred metalloproteinase material according to the invention is selected from products which cleave $\alpha_2$-antiplasmin with a molecular weight of the order of 68,000 daltons to give a peptide which is essentially devoid of $\alpha_2$-AP activity and has an MW of the order of 53,000 daltons.

The metalloproteinase materials which are preferably recommended according to the invention consist of the venoms of *Bitis arietans, Crotalus basiliscus* and *Lachesis muta* (or *Lachesis mutus*).

ω-Amino acids such as AMCHA and EACA are known to favor the conversion of plasminogen to plasmin via two mechanisms: induction of a conformational change from Glu-plasminogen to Lys-plasminogen, which can more readily be activated to form plasmin, and interference with the interaction of plasmin with $\alpha_2$-AP, affording at least a 10-fold decrease in the plasmin-inhibiting effect of $\alpha_2$-AP.

It has now been found, surprisingly, that said ω-amino acids potentiate the desired effect of the metalloproteinase material on $\alpha_2$-AP and $\alpha_2$-M when using a plasma not exhausted in $\alpha_2$-AP, in the presence or absence of PAI. On the other hand, there is no potentiation of the effect of said metalloproteinase material when using a plasma exhausted in $\alpha_2$-AP, since, in this case, the generation of plasmin from plasminogen is sufficient with said metalloproteinase material.

In the case of the determination or assay of tPA, it is recommended according to the invention to incorporate a stimulant. The stimulant which can be used here is a conventional means of the prior art, for example fibrin monomers marketed especially under the tradename DESASIF [des-AA-fibrinogen] by BIOPOOL, fibrinogen fragments (see the afore-mentioned article by VERHEIJEN) marketed especially by DIAGNOSTICA STAGO in its assay kit STACHROM PA, or a polylysine described especially in the afore-mentioned article by GYZANDER.

Advantageously, according to the invention, to determine or assay tPA, it is recommended to use a concentration of venom, in an appropriate buffer, which is greater than or equal to 0.025 mg/ml (corresponding to a final content which is greater than or equal to 0.0125 mg/ml in the test mixture). In practice, the maximum concentration of venom in the buffer will be less than or equal to 1 mg/ml. Preferably, it will be more advantageous to use a concentration of venom in the buffer of the order of 0.05 mg/ml. The buffer will preferably be a phosphate buffer of pH 7.0 to 9.0 and more preferably a phosphate buffer of pH 7.5. Said buffer can contain bovine albumin (BSA) in order to favor the lyophilization of the reagents to be incorporated in the assay kits.

To assay or determine PAI, it is advantageously recommended to use a concentration of venom in the plasma of 0.1 to 1 mg/ml and preferably a concentration of 0.24 mg/ml.

According to the best mode of carrying out the invention, to determine or assay tPA, (a) venom is incorporated into the plasma to be studied, diluted in the appropriate buffer, (b) the mixture is incubated at 37° C. for 2 minutes, (c) the means of stimulating the conversion of plasminogen to plasmin (especially the product marketed under the name STIMU-GEN by DIAGNOSTICA STAGO) is added, (d) the mixture is incubated at 37° C. for 150 minutes, (e) the chromogenic substrate is added, and then (f) the mixture is incubated at 37° C. for 5 minutes. The release of the chromogenic means is then read off, particularly at 405 nm, either by a static method called the end-point technique, or by a kinetic method called the two-point technique (acetic acid being added in this case). The reading of the OD (especially by transmission) is checked by a blank test in which the plasma to be studied, to which venom has been added, is replaced with the buffer to which venom has been added.

As a variant, the venom can be incorporated into the system at stage (c) with the stimulant.

Again according to the best mode of carrying out the invention, to determine or assay PAI, (a) tPA or uPA is incorporated into the plasma to be studied, (b) the mixture is incubated at 37° C. for 5 minutes, (c) a mixture consisting of plasminogen, an ω-amino acid (especially AMCHA or EACA) and venom is added, (d) the mixture is incubated at 37° C. for 3 minutes, (e) the chromogenic substrate is added, and then (f) the mixture is incubated at 37° C. for 3 minutes. The release of the chromogenic means is then read off, as indicated above, particularly at 405 nm, by the end-point technique or kinetically by the two-point technique (acetic acid being added in this case). The reading of the OD (especially by transmission) is again checked by a blank test in which the tPA or uPA is replaced with a buffer.

Among the synthetic plasmin-specific chromogenic substrates, it is possible to use one of the following compounds in particular:

H—D—Nva—L—CHA—L—Lys—pNA,
H—D—Abu—L—CHT—L—Lys—pNA,
H—D—Nle—L—CHA—L—Arg—pNA,
H—D—Phe—L—Pip—L—Arg—pNA,
H—D—Val—Leu—Lys—pNA,
MM—L—Phe—L—Arg—pNA,
MM—L—4Hyp—L—Arg—pNA,
MM—L—3Hyp—L—Arg—pNA,
MM—L—Tyr—L—Arg—pNA,
MM—L—Phg—L—Arg—pNA,
MM—L—Hyp—L—Lys—pNA,
MM—L—Pro—L—Lys—pNA,
MM—L—Tyr—L—Lys—pNA,
MM—L—Hyp(OtBu)—L—Arg—pNA,
EM—L—Pro—L—Arg—pNA,
EM—L—Tyr—L—Arg—pNA,
EM—L—Phe—L—Arg—pNA,
EM—L—Phg—L—Arg—pNA,
$PEG_{200}$[CO—D—Glu(OBzl)—L—Pro—L—Arg—pNA]$_2$,
$PEG_{400}$[CO—D—Leu—Gly—L—Arg—pNA]$_2$ (the last two substrates in this list being described in French patent application n° 90 01964 in the name of the Assignee) or one of their addition salts with an acid, especially with HCl, acetic acid or trifluoroacetic acid as the salifying acid.

The assay kit according to the invention will comprise at least one metalloproteinase material preferably selected from the venoms of *Bitis arietans, Crotalus basiliscus, Lathesis muta* and mixtures thereof, and, if appropriate, pure tPA, uPA and/or PAI samples.

The solution according to the invention, which uses a metalloproteinase material for inhibiting the plasma proteases $\alpha_2$-AP and/or $\alpha_2$-M, is suitable for the assay of tissue and urokinase plasminogen activators and their inhibitors. The solution according to the invention is more particularly intended for the assay or determination of tPA and its inhibitor, PAI.

EXAMPLE 1 tPA Assay Protocol

The procedure shown in Diagram A above is carried out in a plastic hemolysis tube kept at a temperature of 37° C., in accordance with the modalities given in Table I below.

TABLE I tPA ASSAY

| Ingredient | Test | Blank |
| --- | --- | --- |
| Plasma diluted in a buffer with metalloproteinase material (a) | 200 µl | — |
| Buffer plus metalloproteinase material (a) | — | 200 µl |
| Incubation | 2 minutes | 2 minutes |
| Stimulant (b) | 200 µl | 200 µl |
| Incubation | 150 minutes | 150 minutes |
| Substrate (c) | 200 µl | 200 µl |

Notes
(a) venom of B. arietans, C. basiliscus or L. muta
(b) product marketed under the name STIMUGEN by DIAGNOSTICA STAGO
(c) plasmin-specific chromogenic substrate
Comment
The reading is made with a spectrophotometer for assessing the release of the chromogenic group at 405 nm.

EXAMPLE 2

PAI Assay

The procedure shown in Diagram B above is carried out in a plastic hemolysis tube kept at a temperature of 37° C., in accordance with the modalities given in Table II below.

TABLE II

PAI ASSAY

| Ingredient | Test | Blank |
| --- | --- | --- |
| Plasma | 50 µl | 50 µl |
| uPA or tPA | 200 µl | — |
| Buffer | — | 200 µl |
| Incubation | 5 minutes | 5 minutes |
| Plasminogen plus (a) plus (b) | 200 µl | 200 µl |
| Incubation | 3 minutes | 3 minutes |
| Substrate (c) | 200 µl | 200 µl |
| Incubation | 3 minutes | 3 minutes |

Notes
(a) venom of B. arietans, C. basiliscus or L. muta
(b) ω-amino acid (AMCHA or EACA)
(c) plasmin-specific chromogenic substrate
Comment
The reading is made with a spectrophotometer for assessing the release of the chromogenic group at 405 nm.

EXAMPLE 3

Effect of the Metalloproteinase Material on $\alpha_2$-AP

The $\alpha_2$-AP content of a normal plasma was measured by means of the assay kit "STACHROM $\alpha_2$-AP" marketed by DIAGNOSTICA STAGO, in the presence or absence of a metalloproteinase material consisting of the venom of B. arietans, C. basiliscus or L. muta, the venom being at a concentration greater than or equal to 0.50 mg/ml of plasma in a dilution buffer (i.e. a content greater than or equal to 0.0125 mg/ml of the plasmin-containing mixture).

$\alpha_2$-AP inhibition, measured with four different batches of the venom of B. arietans, four different batches of the venom of C. basiliscus and four different batches of the venom of L. muta, is obtained for concentrations ranging from 0.5 to 1 g/ml of plasma (i.e. 0.025 to 0.050 g/l of buffer) in the case of B. arietans, on the one hand, and for a concentration of 0.5 mg/ml of plasma (i.e. 0.025 mg/ml of buffer) in the case of C. basiliscus or L. muta, on the other.

When assaying $\alpha_2$-AP in a normal plasma ($\alpha_2$-AP content taken to be 100%) in the presence of one of said venoms, a (relative) $\alpha_2$-AP content of about 25% (20 to 30%) is found, which demonstrates inhibition of $\alpha_2$-AP by the metalloproteinase material contained in the venom of B. arietans, C. basiliscus or L. muta.

Figure 2:
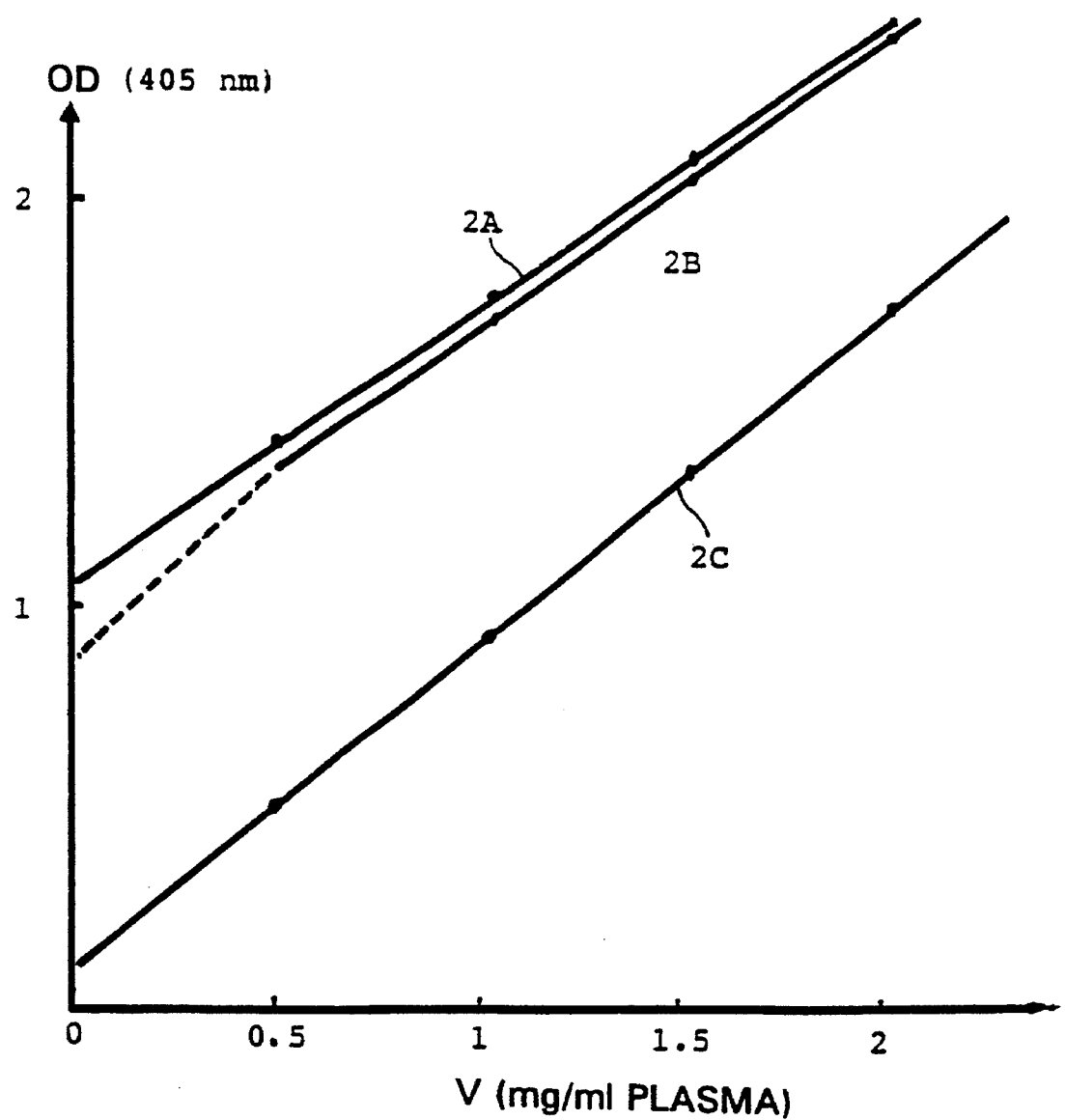
FIG. 2 is a graph of an $\alpha_2$-AP assay.

The results collated in FIG. 2 below, in the system OD (at 405 nm) on the ordinate/V (venom of B. arietans) in mg/ml on the abscissa, confirm the inhibition of $\alpha_2$-AP by said venom, curve 2A corresponding to a sample containing the buffer and plasmin, curve 2B corresponding to a sample containing the plasma and plasmin, and curve 2C corresponding to a sample containing the buffer without plasmin.

EXAMPLE 4

Effect of the Metalloproteinase Material on Plasminogen and Plasmin

It was observed that the metalloproteinase material (especially the venom of B. arietans, C. basiliscus or L. muta) has no effect on plasminogen and that it does not have a statistically significant effect on plasmin. In particular when adding the metalloproteinase material to plasmin and then incubating at 37° C., it is found that the metalloproteinase material is capable of hydrolyzing synthetic plasmin-specific substrates [especially the substrates CBS 30.41 and CBS 10.65, which are H—D—Abu—L—CHA—L—Lysp-NA.AcOH and MM—Hyp—Arg—pNA.AcOH respectively]. This hydrolysis is a function of the concentration of venom; when using a relatively low concentration of venom (0.0125 mg/ml of medium), 95% of the plasmin is active on the substrate: the effect of the venom on plasmin is not therefore statistically significant.

EXAMPLE 5

Effect of the Metalloproteinase Material on uPA and tPA

Figure 3:
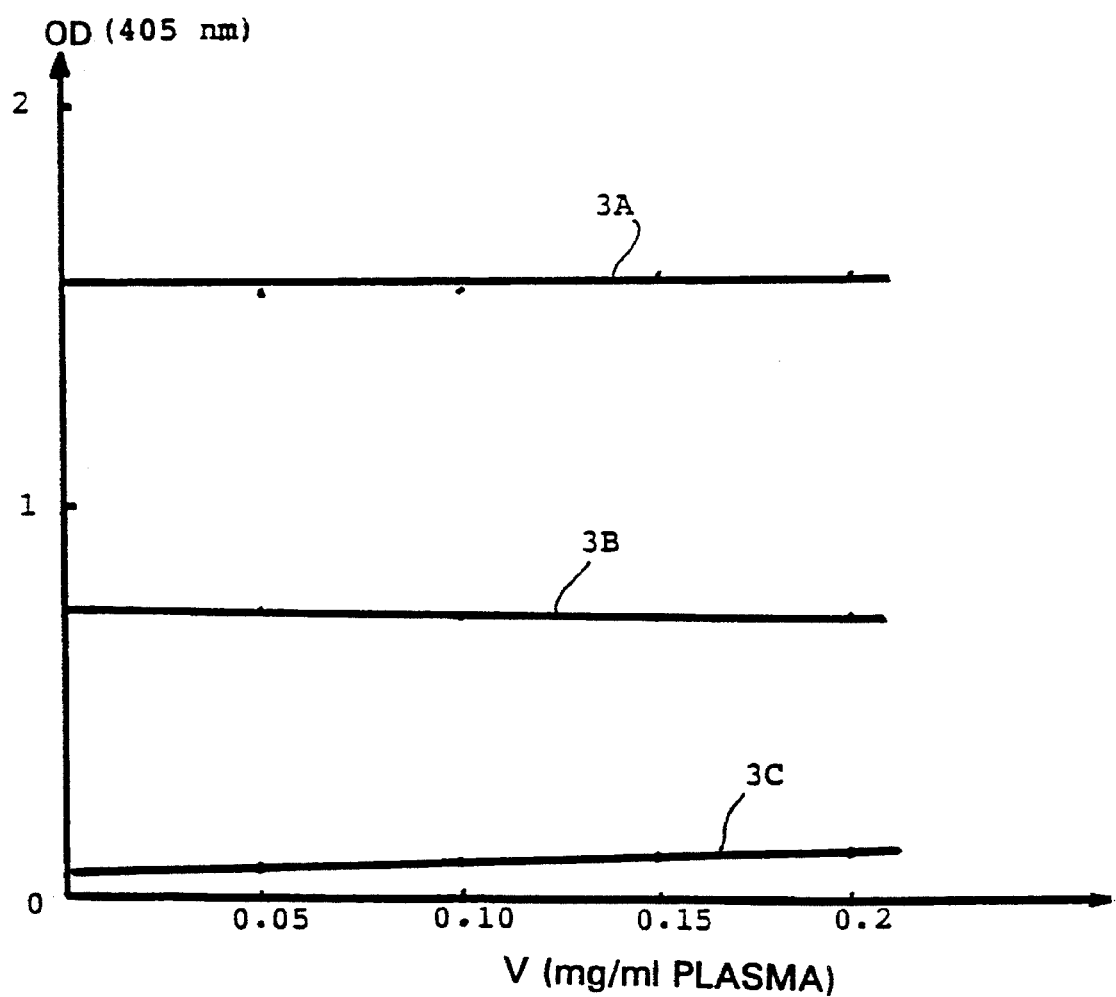
FIG. 3 is a graph of activity of uPA on a specific substrate.

It was observed that the activity of uPA (urokinase) measured directly on a specific substrate is not modified in the presence of venom (see FIG. 3).

Figure 4:
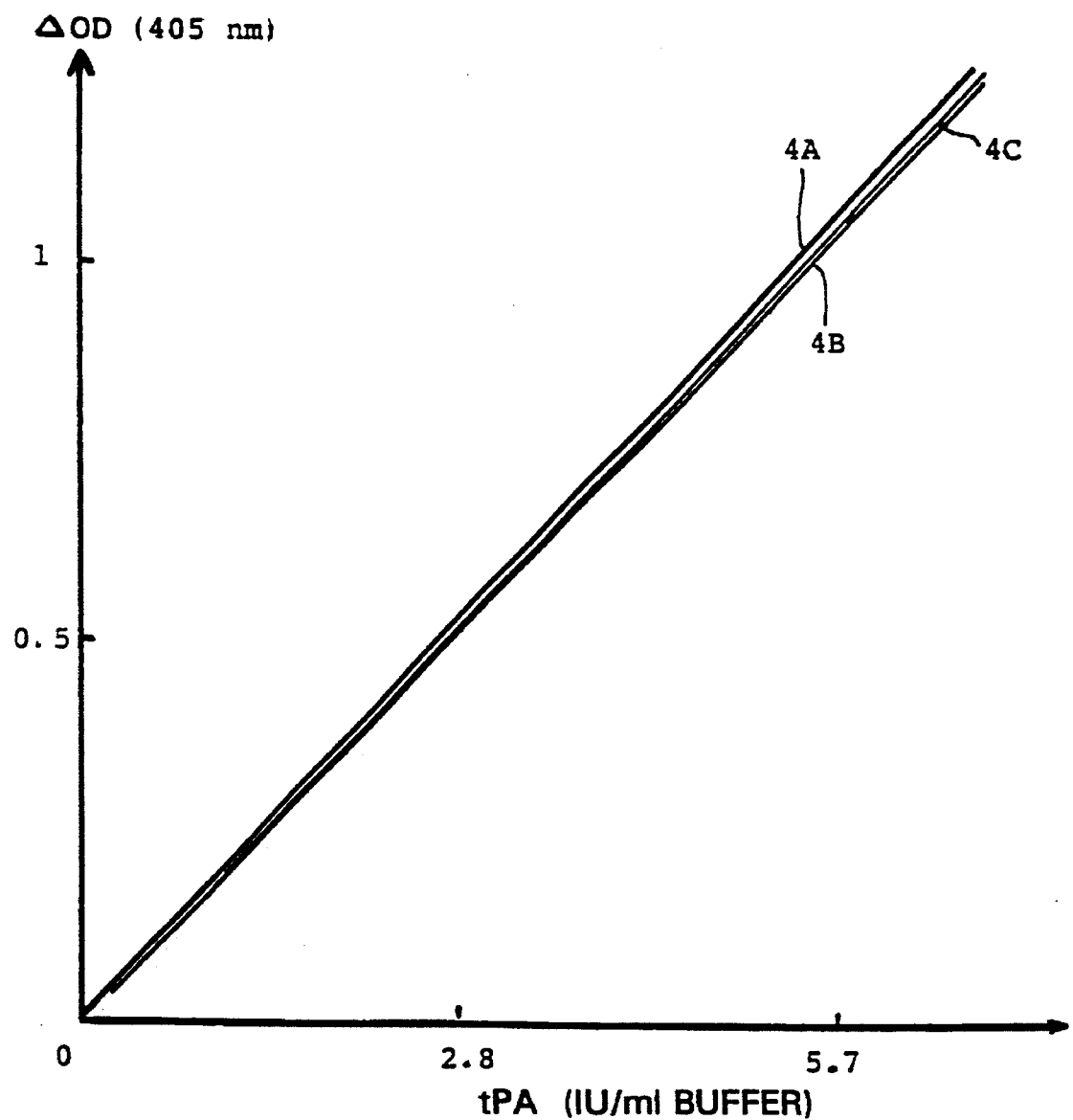
FIG. 4 is a graph of activity of tPA.

It was also observed that the activity of tPA measured by STACHROM PA is not modified in the presence of venom (see FIG. 4).

In FIG. 3, in the system OD (at 405 nm) on the ordinate/V (venom of B. arietans) in mg/ml on the abscissa, curves 3A (uPA at 100 IU/ml), 3B (uPA at 40 IU/ml) and 3C (buffer only) are approximately linear.

In FIG. 4, in the system OD (at 405 nm) on the ordinate/ tPA (in the buffer) in IU/ml on the abscissa, curves 4A (buffer containing 0.24 mg/ml of venom of B. arietans), 4B (buffer containing 0.50 mg/ml of venom of B. arietans) and 4C (buffer without venom) are practically identical straight lines.

EXAMPLE 6

Effect of the Metalloproteinase Material on PAI

Figure 5:
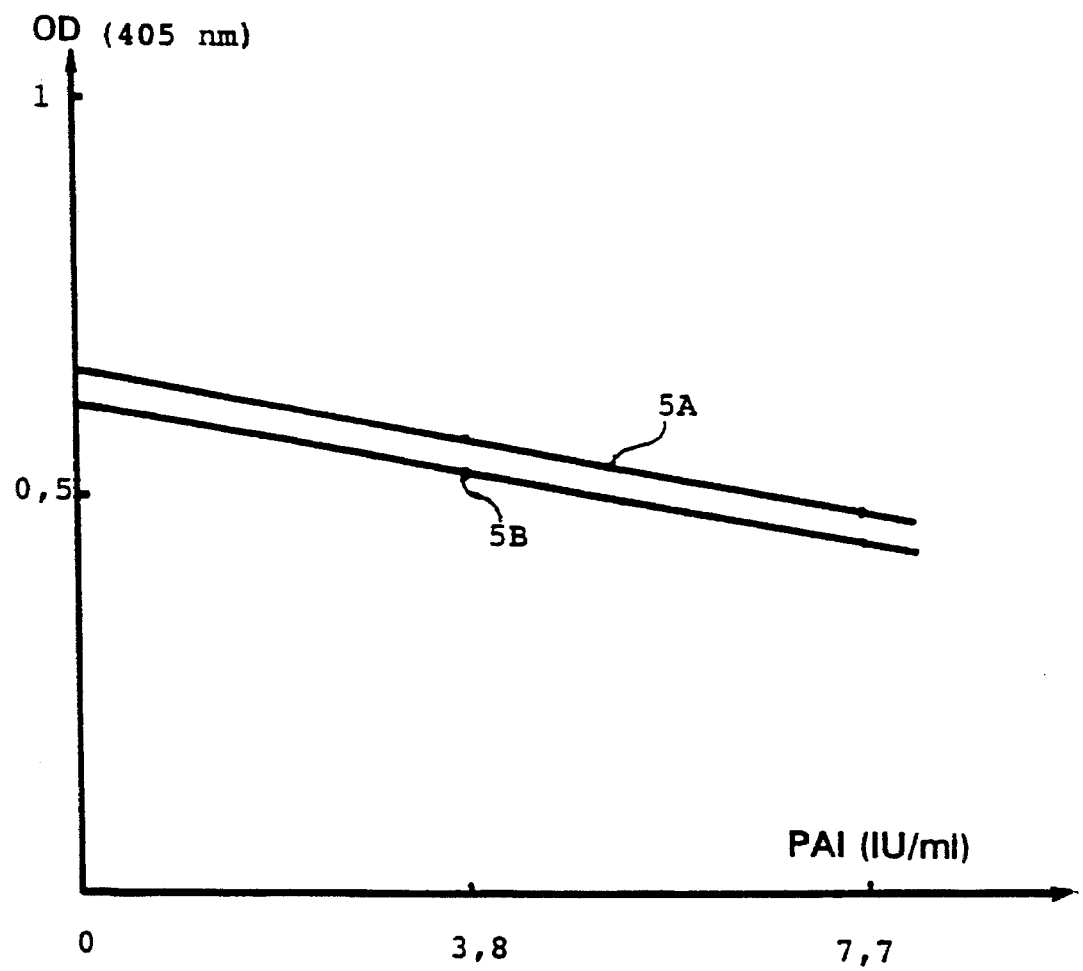
FIG. 5 is a graph of activity of PAI.

It was observed that when a plasma rich in PAI is incubated in the presence of a metalloproteinase material (venom of B. arietans, C. basiliscus or L. muta), the activity of the PAI, as assayed, is identical to that found in said plasma in the absence of said metalloproteinase material (see FIG. 5).

Figure 6:
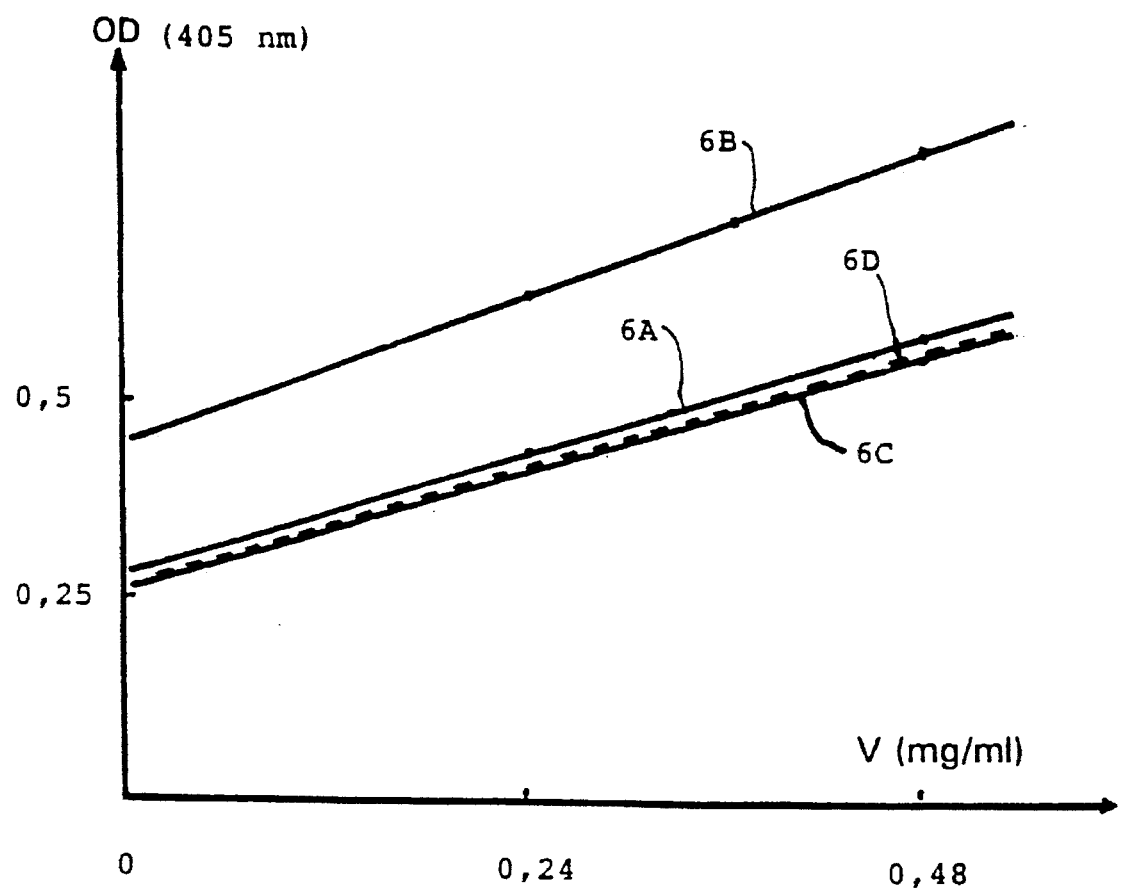
FIG. 6 is a graph of activity of tA.

It was also observed that when adding purified tPA to a mixture of plasma and metalloproteinase material (venom of B. arietans, C. basiliscus or L. muta), the tPA added is totally inhibited by the PAI in the plasma, in the absence and presence of said metalloproteinase material (see FIG. 6).

Taken together, these results clearly demonstrate that, according to the invention, the metalloproteinase material does not inhibit PAI.

In FIG. 5, in the system OD (at 405 nm) on the ordinate/ PAI in IU/ml on the abscissa, curves 5A (PAI in the absence of venom of B. arietans) and 5B (PAI in the presence of venom of B. arietans) are parallel straight lines.

In FIG. 6, in the system OD (at 405 nm) on the ordinate/ venom (of B. arietans) in mg/ml on the abscissa, tPA was added to a plasma P0 (PAI content of 0 IU/ml) depleted in PAI, or to a plasma P1 (PAI content of 7.7 IU/ml) rich in PAI, in the presence of increasing venom concentrations of 0 to 0.50 mg/ml. Curve 6A (plasma P0 without tPA) is a straight line which is approximately parallel to straight line 6B (buffer P0 plus tPA at 5.2 IU/ml). Straight lines 6C (plasma P1 without tPA) and 6D (plasma P1 plus tPA at 5.2 IU/ml) are identical; this indicates that the tPA added to the plasma (P1) rich in PAI is inhibited in the absence or presence of venom.

EXAMPLE 7

Effect of the Metalloproteinase Material on uPA-PAI Complexes

Any interaction of the metalloproteinase material (crude venom of B. arietans, as collected and supplied by the stock farms) with the uPA-PAI complexes formed by incubating a plasma rich in PAI (plasma P2 containing PAI at a concentration of 10 IU/ml) with uPA (urokinase) at 37° C. for 0.25 h was assessed by comparison with plasma P0 exhausted in PAI, used in Example 6.

The results obtained with the venom of B. arietans have been collated in Tables III and IV below. Said results show that there is no complex formation in plasma P0 because there is no PAI: all the residual uPA therefore remains; as plasma P2 contains 10 IU/ml of PAI, there is complex formation with uPA and only part of the added uPA remains. These results also show that the venom has no effect on the dissociation of the uPA—PAI and tPA—PAI complexes.

EXAMPLE 8

Figure 7:
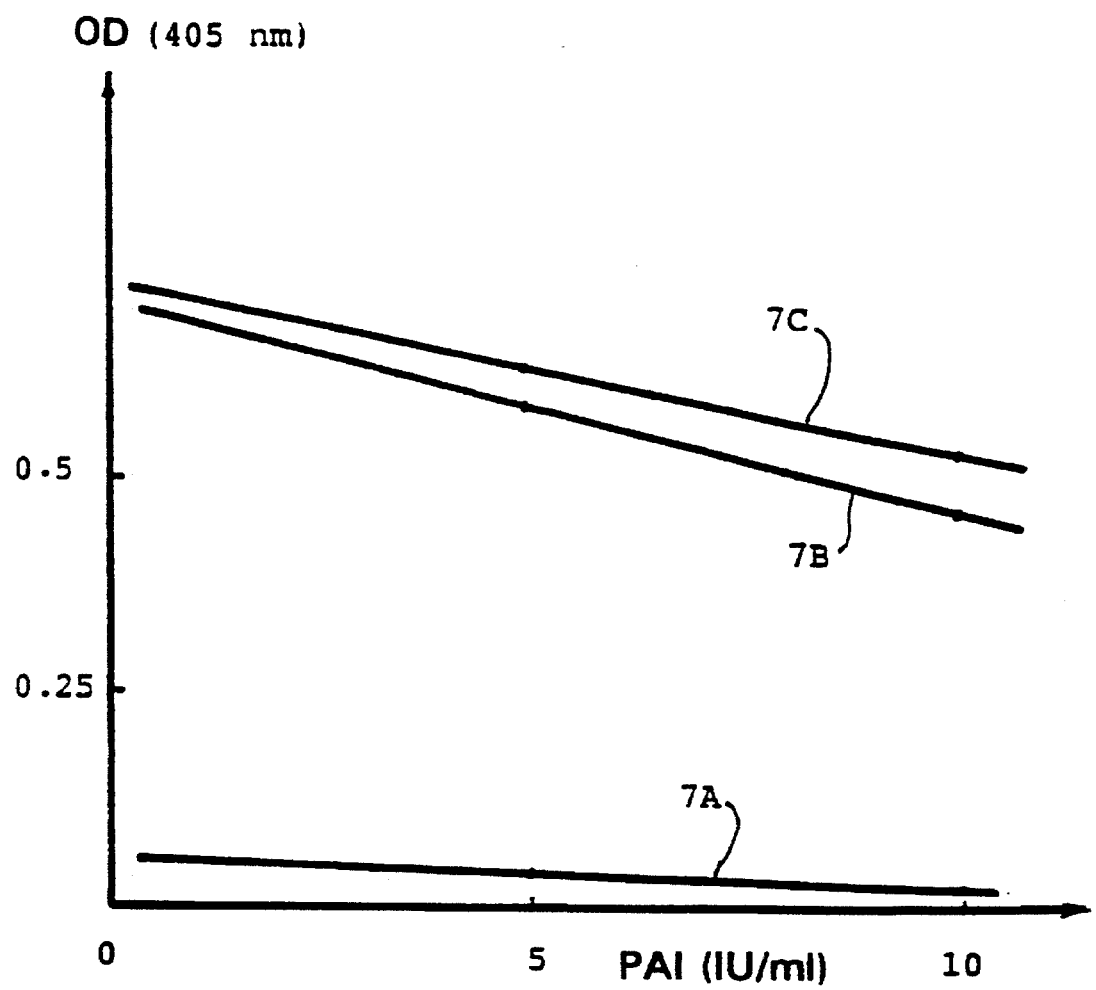
FIG. 7 is a graph of plasmin generation in an assay of PAI.

Effect of the Metalloproteinase Material and AMCHA on the Conversion of Plasminogen to Plasmin by uPA or tPA Firstly, a check was carried out to ensure that AMCHA, the reference omega-amino acid, increases the generation of plasmin in the assay of PAI in the presence of urokinase (see the results given in FIG. 7).

In FIG. 7, in the system OD (at 405 nm) on the ordinate/ PAI in IU/ml on the abscissa, the curves obtained, namely 7A (without AMCHA), 7B (AMCHA at 1.3 mmol/l in the reagent) and 7C (AMCHA at 2.6 mmol/l in the reagent), are straight lines and show that AMCHA does indeed increase the conversion of plasminogen to plasmin.

Secondly, it was desirable to check that AMCHA reduces the effect of $\alpha_2$-AP in a normal plasma (i.e. a plasma with an $\alpha_2$-AP content of 100%). According to the afore-mentioned "STACHROM $\alpha_2$-AP" method, it was found that the average $\alpha_2$-AP level is 30% at a concentration of 0.88 mmol/l of dilution buffer.

Thirdly, as the crude venom (venom of B. arietans) is capable of inhibiting $\alpha_2$-AP in the plasma, either directly or by interfering with the $\alpha_2$-AP/plasmin interaction, an attempt was made to see whether this effect is potentiated by AMCHA according to the following modalities.

In the assay of $\alpha_2$-AP by "STACHROM $\alpha_2$-AP", an $\alpha_2$-AP content of less than 5% is found in a plasma incubated in the presence of venom and AMCHA added simultaneously. This observation allows the conclusion that AMCHA potentiates the effect of the venom on the inhibition of $\alpha_2$-AP.

In the assay of PAI, it is found that the venom has a very large effect on the increase in the generation of plasmin and that this effect is greater than that of AMCHA (see Tables V, VI and VII below). The effect of the venom is found to be potentiated by AMCHA in the presence or absence of PAI (see said Tables V, VI and VII).

When using a plasma deficient in $\alpha_2$-AP, the generation of plasmin is substantial with the venom and even more so with AMCHA. This result is associated with the conversion of Glu-plasminogen to Lys-plasminogen and it is found that AMCHA does not potentiate the venom in this case (see Table VIII below).

EXAMPLE 9

Effect of the Metalloproteinase Material on $\alpha_2$-M

It is known that substances such as EACA stimulate in vitro the generation of thrombin in a plasma, whereas the effect of $\alpha_2$-M is inhibited [q.v. I. G. SLOAN et al., Thromb. Res., 44, pages 761–769, (1986)]. This phenomenon can be explained by the fact that omega-amino acids such as EACA and AMCHA possess a terminal amine group and are capable of inhibiting $\alpha_2$-AP by means of this terminal amine group, since compounds such as methylamine are known to act in this way.

It is further known that certain venoms have been said to lose their proteolytic activity when incubated with $\alpha_2$-M. It is also known, however, that the complexation of $\alpha_2$-M with venom proteinases can be retarded in the presence of a substrate for proteinases such as $\alpha_2$-M [see the aforementioned article by L. F. KRESS].

In view of these circumstances, it was desirable to check whether or not a metalloproteinase material such as a venom (crude venom of B. arietans), if appropriate in association with an omega-amino acid (AMCHA), could have a favorable effect in the assay of PAI. With this in mind, the residual plasmin after inhibition by aprotinin was measured. It was observed that:

aprotinin (0.1 TIU/ml) inhibits the purified plasmin but not the venom, the plasmin generated in the presence of aprotinin is about 3% in a buffered system, and the content of plasmin generated in a plasma medium and bound to $\alpha_2$-M is less than 5%, even in the absence of $\alpha_2$-AP.

The result is that the interference by $\alpha_2$-M is therefore negligible, even in the absence of $\alpha_2$-AP.

The results obtained are collated in Tables IX and X below. Table IX relates to measurement of the plasmin generated in the presence of urokinase (UPA), on the one hand, and in the presence or absence of aprotinin, on the other, in a plasma which is normal in $\alpha_2$-AP but depleted in PAI. Table X relates to measurement of the plasmin generated in the presence of urokinase, on the one hand, and in the presence or absence of aprotinin, on the other, in a plasma depleted in $\alpha_2$-AP.

EXAMPLE 10

Optimum Conditions for tPA Assay

The optimum conditions for tPA assay are obtained with concentrations of venom (preferably crude venom of B. arietans, as collected and supplied by the stock farms) which are:

greater than 0.0125 mg/ml in the reaction mixture (i.e. greater than 0.025 mg/ml in the buffer), and more preferably of the order of 0.025 mg/ml in the reaction mixture (i.e. 0.050 mg/ml in the buffer), whatever the batch of venom.

The optimum generation of plasmin is obtained in 2.50 h for a tPA range of 0 to 4 IU/ml in glass or plastic tubes. The resulting calibration curve is linear (see curve 8A of FIG. 8). The curve obtained with a plasma rich in tPA and diluted in plasma depleted in tPA and PAI is also linear (see curve 8B of FIG. 8).

Figure 8:
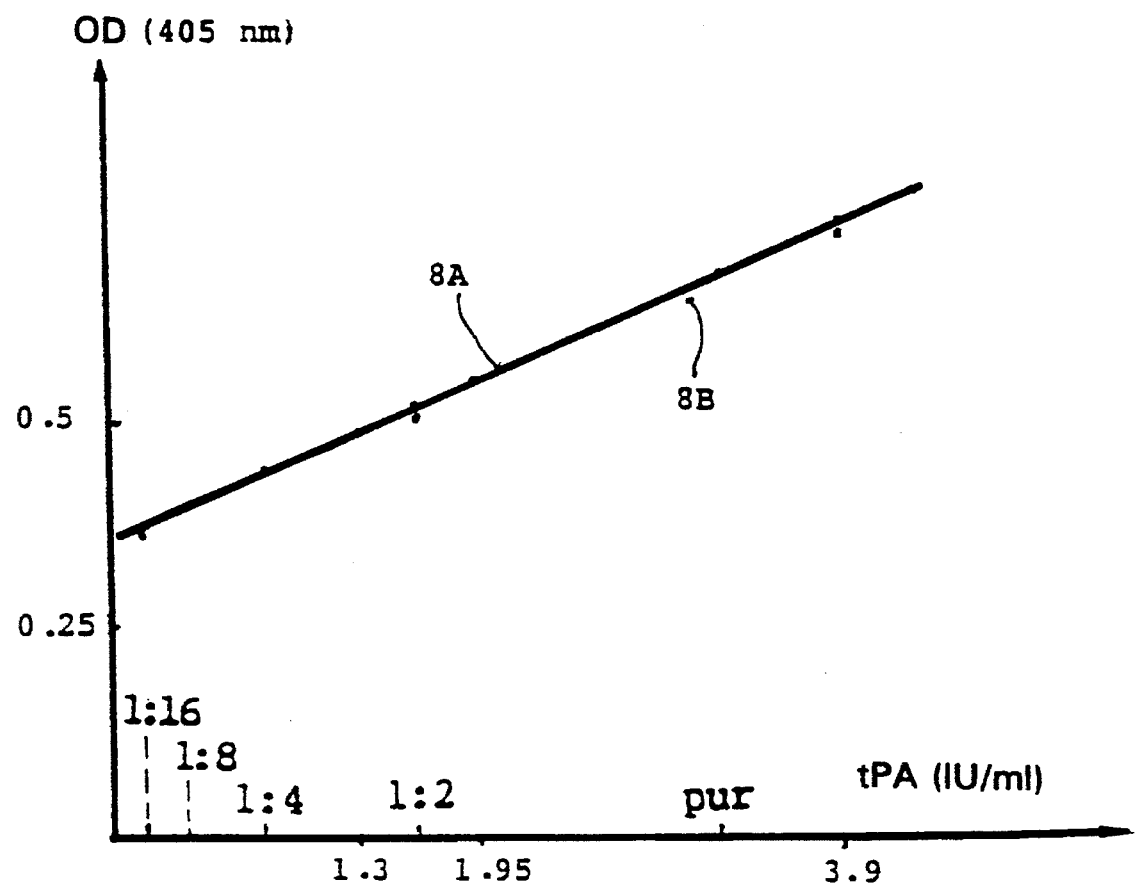
FIG. 8 is a graph of plasmin generation in a tPA assay.

FIG. 8 was obtained in the system OD (at 405 nm) on the ordinate/tPA in IU/ml on the abscissa.

The results observed for plasmas obtained after venous stasis are similar, in the presence of venom, to those observed for euglobulins in the absence of venom (see Table XII below).

Before venous stasis, the results are higher for the euglobulins because the tPA measurement is evaluated with the other plasminogen activators, especially those associated with the route dependent on Factor XII. These other activators are activated during the manufacture of the euglobulins.

EXAMPLE 11

Optimum Conditions for PAI Assay

The optimum conditions for PAI assay are obtained with concentrations of:

uPA of 10 to 50 IU/ml (preferably 10 IU/ml) or tPA (according to the assay by means of "STACHROM PAI"), plasminogen of 1 to 4 U/ml (preferably 3 U/ml) of reaction mixture, whatever the batch of plasminogen, AMCHA of 0.4 to 4 mmol/l (preferably 0.8 mmol/l) of reaction mixture, or any other omega-amino acid, venom (preferably crude venom of B. arietans) of 0.1 to 1 mg/ml of plasma and preferably 0.24 mg/ml of plasma, and substrate (plasmin-specific) of 1 to 5 micromol/ml of plasma and preferably 3.5 micromol/ml of plasma.

Figure 9:
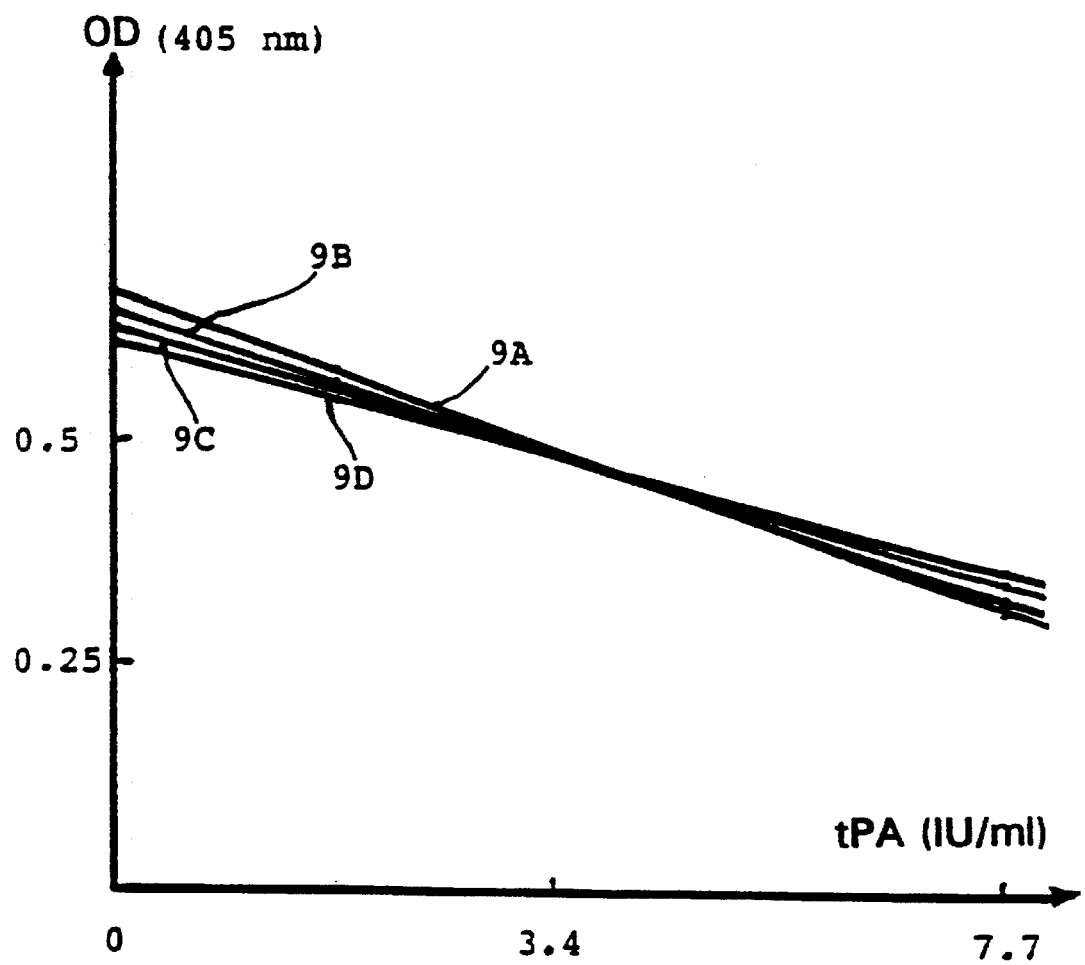
FIG. 9 is a graph of plasmin generation in a plasma containing different amounts of PAI.

Under these conditions, the optimum generation of plasmin is obtained in 3 minutes and hydrolysis of the substrate is effected in 3 minutes. The calibration curve produced with a plasma depleted in PAI [plasma in which the PAI content is zero (PAI=0 IU/ml)] and a plasma rich in PAI (PAI=7.7 IU/ml) is linear (see FIG. 9). In FIG. 9, in the system OD (at 405 nm) on the ordinate/PAI in IU/ml on the abscissa, straight lines 9A, 9B, 9C and 9D were obtained with four different batches of venom of B. arietans.

The results observed for normal plasmas and pathological plasmas (pregnant women and postoperative patients) are similar to those found by the "STACHROM PAI" technique. The units are expressed in IU/ml of urokinase for PAI in the presence of venom and in IU/ml of tPA for PAI by the "STACHROM PAI" technique (see Table XI). However, a small difference is found in pregnant women because PAI-2 has an anti-uPA activity which is greater than the anti-tPA activity (see plasma F).

USE OF THE REAGENTS

In carrying out the invention, it is recommended to use the reagents according to the following modalities:

tPA assay

The following will be used:

the reagents of the assay kit "STACHROM PA" from DIAGNOSTICA STAGO, and a metalloproteinase material (consisting of snake venom) lyophilized alone or lyophilized with "STIMUGEN".

The reconstitution of the bottle is therefore identical to that described in the leaflet "STACHROM PA". The excipients for lyophilization of the metalloproteinase material are those described for "STIMUGEN".

PAI assay

The following will be used:

tPA: reagent of the assay kit "STACHROM PAI" from DIAGNOSTICA STAGO, uPA (urokinase): 20 IU/bottle, to be taken up with 2 ml of distilled water, lyophilization excipients: phosphate buffer (100 mM; pH 9.0) and BSA at 5 g/l, preservative: gentamicin at 50 mg/l, reagent, to be taken up with 2 ml of distilled water:
  1 volume of purified plasminogen in phosphate buffer at pH 7.5,
  3 volumes of metalloproteinase material (snake venom) at a concentration of 0.15 mg/ml in distilled water, and
  2 volumes of AMCHA at 4 mmol/l in a diluent containing a phosphate buffer (50 mM; pH 7.5), 3% of glycine and 0.9% of NaCl (preservative: gentamicin at 50 mg/l), substrate: 16.5 micromol/bottle, to be taken up with 2 ml of distilled water, in conventional glycine excipient, and standard or control plasma lyophilized in a medium comprising 3% of glycine, 1% of lactose, 1% of sucrose and 50 mg/l of gentamicin.

TABLE III uPA assay

| uPA added (IU/ml) | On plasma P0 Residual uPA (IU/ml) | | On plasma P2 Residual uPA (IU/ml) | |
|---|---|---|---|---|
| | Theoretical | Found | Theoretical | Found |
| 20 | 20 | 20 | 10 | 10 |
| 28 | 28 | 27 | 18 | 16.2 |
| 35 | 35 | 32 | 25 | 23.2 |

TABLE IV

PAI assay

| uPA added (IU/ml) | PAI (IU/ml) On plasma P0 | | PAI (IU/ml) On plasma P2 | |
|---|---|---|---|---|
| | Theoretical | Found | Theoretical | Found |
| 20 | 0 | 0 | 10 | 10 |
| 28 | 0 | 1 | 2 | 1.8 |
| 35 | 0 | 3 | 0 | 1.8 |

TABLE V

PAI assay ($\Delta$OD) on plasma P0 (PAI = 0 IU/ml)

| | Without AMCHA | AMCHA (4 mmol/l) | AMCHA (8 mmol/l) |
|---|---|---|---|
| Without venom | 57 | 709 | 724 |
| Venom (0.25 mg/ml) | 776 | 1012 | 944 |
| Venom (0.50 mg/ml) | 625 | 1030 | 931 |

TABLE VI

PAI assay ($\Delta$OD) on plasma P3 (PAI = 8 IU/ml)

| | Without AMCHA | AMCHA (4 mmol/l) | AMCHA (8 mmol/l) |
|---|---|---|---|
| Without venom | 33 | 473 | 538 |
| Venom (0.25 mg/ml) | 452 | 663 | 614 |

TABLE VII

PAI assay ($OD_{P3} - OD_{P0}$)

Slope obtained

| | Without AMCHA | AMCHA (4 mmol/l) | AMCHA (8 mmol/l) |
|---|---|---|---|
| Without venom | 24 | 236 | 186 |
| Venom (0.25 mg/ml) | 324 | 349 | 330 |

TABLE VIII

PAI assay ($\Delta$OD) on plasma deficient in $\alpha_2$-AP

| | Without AMCHA | AMCHA (8 mmol/l) |
|---|---|---|
| Without venom | 433 | 1505 |
| With venom (0.25 mg/ml) | 1345 | 1468 |

TABLE IX

| $\Delta$OD | BUFFER without aprotinin | BUFFER with aprotinin | PLASMA P0 (PAI = 0 IU/ml) without aprotinin | PLASMA P0 (PAI = 0 IU/ml) with aprotinin |
|---|---|---|---|---|
| With venom | 852 | 23 (2.7%) | 257 | 0 (0%) |

TABLE X

| $\Delta$OD | BUFFER without aprotinin | BUFFER with aprotinin | PLASMA DEFICIENT in $\alpha_2$-AP without aprotinin | PLASMA DEFICIENT in $\alpha_2$-AP with aprotinin |
|---|---|---|---|---|
| Without venom | 1764 | 216 (12%) | 1645 | 181 (11%) |
| With venom | 1774 | 231 (13%) | >2.0 | 279 — |

TABLE XI

| Plasma | PAI (IU/ml) STACHROM PAI | PAI (IU/ml) Urokinase and venom |
|---|---|---|
| A | 0 | 0 |
| B | 0 | 0.2 |
| C | 18.3 | 6.0 |
| D | 18.7 | 6.5 |
| E | 23.2 | 8.5 |
| F | 16.6 | 7.9 |

TABLE XII

| Sample | tPA (IU/ml) Euglobulins in the absence of venom | tPA (IU/ml) Plasma in the presence of venom |
|---|---|---|
| Normal pool | <0.1 | <0.1 |
| Plasma G before venous stasis | <0.88 | <0.1 |
| Plasma G after venous stasis | 3.6 | 3.7 |

What is claimed is:

1. In a method of determining (i) a plasminogen activator selected from the group consisting of tissue plasminogen activators (tPAs) and urokinase plasminogen activators (uPAs), and (ii) an inhibitor (PAI) of said plasminogen activator, said method comprises conversion of plasminogen to plasmin and assay of the plasmin resulting from said conversion, wherein the improvement comprises inhibiting at least one of the plasma proteins $\alpha_2$-antiplasmin and $\alpha_2$-macroglobulin by contact thereof with a metalloproteinase material selected from the group consisting of the venoms of *Bitis arietans, Crotalus basiliscus* and *Lachesis muta*.

2. A method according to claim 1, T1 combining said metalloproteinase material with at least one ω-amino acid.

3. A method according to claim 1, further comprising determining PAI by (a) incorporating tPA or uPA into the plasma before assaying, (b) incubating the mixture, (c) adding a mixture consisting of plasminogen, an ω-amino acid and said metalloproteinase material, (d) incubating the mixture, (e) adding a plasmin-specific chromogenic substrate, and (f) incubating the mixture, and reading the optical density corresponding to the release of the chromogenic means being effected by comparison with a blank test wherein the plasminogen activator (tPA or uPA) is replaced with a buffer at stage (c).

4. A method according to claim 1 further comprising effecting assay of the plasmin resulting from said conversion by combining the plasmin with a plasmin-specific chromogenic substrate.

5. A method according to claim 1, further comprising determining tPA by (a) incorporating the metalloproteinase material into the plasma before assaying, diluting in the appropriate buffer, (b) incubating the mixture, (c) adding a means of stimulating the conversion of plasminogen to plasmin, (d) the mixture is incubated, (e) adding a plasmin-specific chromogenic substrate and (f) incubating the mixture, and reading the optical density corresponding to the release of the chromogenic means being effected by comparison with a blank test wherein the plasma to which metalloproteinase material of stage (a) has been added, is replaced with a buffer to which metalloproteinase material has been added.

6. A method according to claim 5 comprising incorporating the metalloproteinase material at stage (c) instead of stage (a).

7. A method according to claim 5, wherein the concentration of the metalloproteinase material in the plasma is 0.01 to 0.5 mg/ml.

8. A method according to claim 3, wherein the concentration of the metalloproteinase material is 0.1 to 1 mg/ml of plasma.

* * * * *